United States Patent
Agrawal et al.

(10) Patent No.: US 11,267,768 B2
(45) Date of Patent: Mar. 8, 2022

(54) METHANE ETHANE CRACKERS

(71) Applicant: PURDUE RESEARCH FOUNDATION, West Lafayette, IN (US)

(72) Inventors: Rakesh Agrawal, West Lafayette, IN (US); Peter Oladipupo, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 0 days.

(21) Appl. No.: 16/832,092

(22) Filed: Mar. 27, 2020

(65) Prior Publication Data

US 2020/0308086 A1    Oct. 1, 2020

Related U.S. Application Data

(60) Provisional application No. 62/826,325, filed on Mar. 29, 2019.

(51) Int. Cl.
*C07C 4/04* (2006.01)
*C07C 4/06* (2006.01)
*C07C 5/333* (2006.01)
*B01J 8/06* (2006.01)
(Continued)

(52) U.S. Cl.
CPC .............. *C07C 4/04* (2013.01); *B01J 8/062* (2013.01); *B01J 8/065* (2013.01); *B01J 8/085* (2013.01); *B01J 8/1827* (2013.01); *C07C 4/06* (2013.01); *C07C 5/333* (2013.01); *B01J 2208/00504* (2013.01); *B01J 2208/065* (2013.01)

(58) Field of Classification Search
CPC ........... C07C 5/333; C07C 11/04; C07C 4/04; C07C 4/06; B01J 19/2415; B01J 2208/00504; B01J 2208/065; B01J 2219/00159; B01J 8/062; B01J 8/065; B01J 8/085; B01J 8/1827
See application file for complete search history.

(56) References Cited

U.S. PATENT DOCUMENTS

| 4,494,485 A | 1/1985 | Kendall et al. |
| 5,254,788 A * | 10/1993 | Gartside .............. B01J 8/003 585/659 |

(Continued)

OTHER PUBLICATIONS

International Search Report and Written Opinion for International Application No. PCT/US2020/025150, dated Jun. 18, 2020.

*Primary Examiner* — Sharon Pregler
(74) *Attorney, Agent, or Firm* — Edmonds & Cmaidalka, P.C.

(57) ABSTRACT

A process for producing olefins by cracking paraffins in the presence of methane. In the conventional steam cracking processes for olefin production, steam is used as a diluent in the feed mixture to the thermal cracker. In the processes provided herein, methane replaces steam as a diluent in the feed mixture to the thermal cracker. Replacing steam with methane as a diluent has a potential for cost savings in the construction and operation of a thermal cracking plant for olefin production. In addition, it leads to a much simpler cracking process compared to the conventional steam cracking technology as in the state of the art.

20 Claims, 6 Drawing Sheets

(51) Int. Cl.
 *B01J 8/08* (2006.01)
 *B01J 8/18* (2006.01)

(56) References Cited

U.S. PATENT DOCUMENTS

2009/0143631 A1 6/2009 Gracey et al.
2013/0158327 A1* 6/2013 Leonard ................. C07C 5/333
 585/655

* cited by examiner

Figure 1: Prior Art

METHANE ETHANE CRACKERS

CROSS-REFERENCE TO RELATED APPLICATIONS

This application claims priority to U.S. Provisional Patent application having Ser. No. 62/826,325, filed on Mar. 29, 2019. The entirety of which is incorporated by reference herein.

GOVERNMENT LICENSE RIGHTS

This invention was made with government support under Cooperative Agreement No. EEC-1647722 awarded by the National Science Foundation. The government has certain rights in the invention.

BACKGROUND OF THE INVENTION

Field of the Invention

Embodiments provided herein relate to systems and processes for converting paraffins (saturated hydrocarbons) to olefins (unsaturated hydrocarbons). More particularly, such embodiments relate to systems and processes for dehydrogenation.

Description of the Related Art

Steam cracking is a commercial process for the thermal cracking of paraffins to produce olefins and is well known in the art and is as shown in FIG. 1. It involves passing a preheated feed mixture comprising one or more paraffins and steam through a furnace-fired tubular reactor with radiant coils of the type depicted in FIG. 2, wherein cracking reactions take place. These cracking reactions occur very quickly with reactor residence time of 0.08 seconds-0.5 seconds at high temperatures of 800° C.-900° C. and pressures of 1.7 Bar-2.5 Bar within the radiant coil sections of the furnace, as reported by Sadrameli S. M. in "*Thermal/Catalytic Cracking of Hydrocarbons for the Production of Olefins: A State-of-the-art Review 1—Thermal Cracking Review*" (a paper published in *Fuel* in 2014).

The paraffin feed to the steam cracker typically includes ethane, propane, butane, liquified petroleum gas, naphtha, and gas oil. The incoming feed is typically preheated to temperatures of 500° C.-680° C. and then mixed with steam before being passed through the radiant coil sections of a furnace where the cracking reactions take place. Steam serves to reduce the paraffin feed partial pressure, which helps to achieve increased reactant conversion. Steam to paraffin hydrocarbon ratios typically vary from 0.25-0.85 Kg Steam/Kg hydrocarbon.

Although some other competing reactions occur during the thermal cracking process, paraffin dehydrogenation is the dominant reaction inside the reactor tubes (radiant coils) and is primarily responsible for olefin production. Dehydrogenation of paraffin (especially light alkanes such as ethane) is a highly endothermic process, requiring a lot of heat energy at fairly high temperatures to achieve adequate conversions. The product mixture exiting the steam cracker is cooled very rapidly in transfer line exchangers to a temperature of 350° C.-650° C. to limit degradation by secondary reactions. These product mixtures can vary widely in composition depending on the feedstock to the cracker and the operating conditions therein. The product mixture is typically separated into the desired olefin products using a sequence of physical and chemical separation steps.

Methane is an undesired byproduct of the dehydrogenation process and is typically separated from the steam cracker exhaust stream. When a feedstock already contains methane, an additional separation step is required to remove it prior to sending the feed to the steam cracker. Consequently, methane is removed in two different stages—before and after reaction—contributing to process complexities and costs. In the same vein, process requirements such as water conditioning for steam generation, water boiling, steam superheating, and high-pressure steam superheating prior to its introduction in the feed as well as steam condensation separation subsequent to the cracking reaction contribute very significantly to the process complexities and the capital and operating costs associated with the process.

There is a need, therefore, for a new thermal cracking process that can be operated without steam and that minimizes separation steps for removing methane.

SUMMARY OF THE INVENTION

The processes provided herein provides for the conversion of paraffinic hydrocarbon compounds (or paraffins) to olefinic compounds in the absence of steam. Methane replaces steam as a diluent to lower the paraffin feed partial pressure. Depending on feed composition, typical operating conditions for the processes provided herein include temperatures of 500° C.-1000° C., pressures of 1 atm-30 atm, and methane concentration in the feed mixture is within 10 mol %-95 mol %, preferably within 30 mol %-90 mol % and most preferably within 50 mol %-90 mol %.

In one embodiment, an incoming feed rich in methane and one or more paraffins is sent to a thermal cracker for olefin production.

In another embodiment, an incoming feed rich in methane and one or more paraffins is sent to a catalyst bed-containing cracker, for olefin production. The presence of the catalyst bed is to serve the purpose of enhancing the rate of desired reactions and/or suppress undesired reactions in the cracker.

The processes provided herein eliminate the complexity and expense for steam generation that are associated with conventional steam crackers. If there would ever be need for steam in implementing the processes provided herein, the quantity of steam compared to the quantity of methane would be minimal.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments. It is emphasized that the figures are not necessarily to scale and certain features and certain views of the figures can be shown exaggerated in scale or in schematic for clarity and/or conciseness.

DETAILED DESCRIPTION

Figure 1:
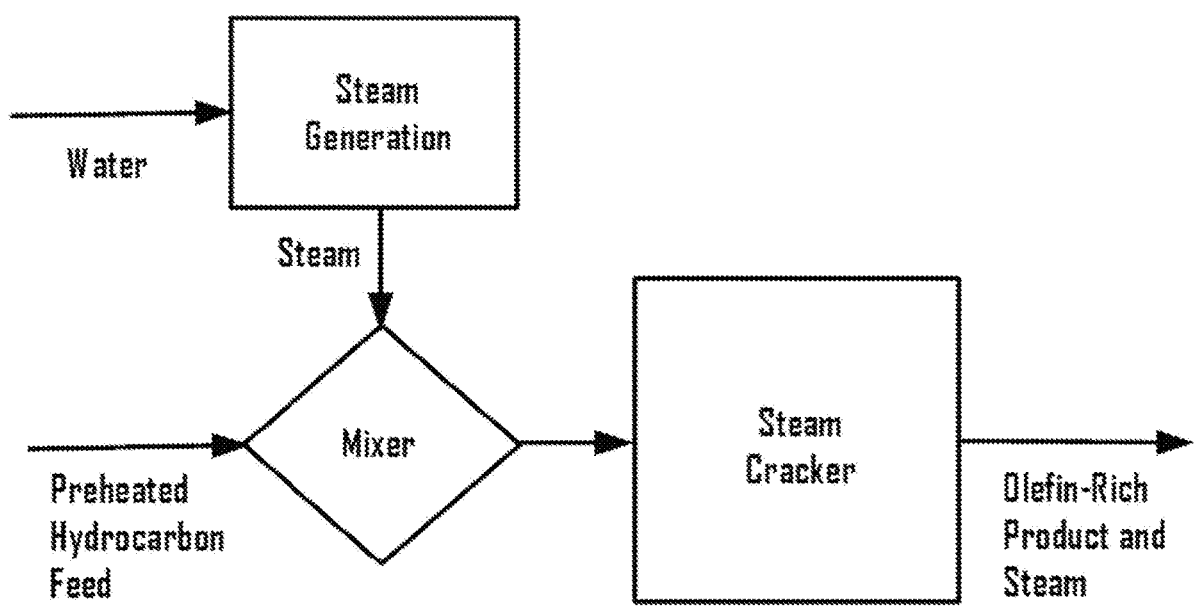
FIG. 1 is a most basic form of a prior art process for conventional steam cracking. This figure provides a block diagram for the essential steam generation and thermal cracking steps that are associated with the steam cracker.

It is to be understood that the following disclosure describes several exemplary embodiments for implementing different features, structures, or functions of the invention. Exemplary embodiments of components, arrangements, and configurations are described below to simplify the present disclosure; however, these exemplary embodiments are provided merely as examples and are not intended to limit the scope of the invention. Additionally, the present disclosure can repeat reference numerals and/or letters in the various exemplary embodiments and across the Figures provided herein. This repetition is for the purpose of simplicity and clarity and does not in itself dictate a relationship between the various exemplary embodiments and/or configurations discussed in the Figures. The exemplary embodiments presented below also can be combined in any combination of ways, i.e., any element from one exemplary embodiment can be used in any other exemplary embodiment, without departing from the scope of the disclosure.

Additionally, certain terms are used throughout the following description and claims and have the specific meanings provided below. As one skilled in the art will appreciate, various entities can refer to the same component by different names, and as such, the naming convention for the elements described herein is not intended to limit the scope of the invention, unless otherwise specifically defined herein. Further, the naming convention used herein is not intended to distinguish between components that differ in name but not function.

In the following discussion and in the claims, the terms "including" and "comprising" are used in an open-ended fashion, and thus should be interpreted to mean "including, but not limited to." The phrase "consisting essentially of" means that the described/claimed composition does not include any other components that will materially alter its properties by any more than 5% of that property, and in any case, does not include any other component to a level greater than 3 wt %.

The term "or" is intended to encompass both exclusive and inclusive cases, i.e., "A or B" is intended to be synonymous with "at least one of A and B," unless otherwise expressly specified herein.

The indefinite articles "a" and "an" refer to both singular forms (i.e., "one") and plural referents (i.e., one or more) unless the context clearly dictates otherwise.

The term "acid gases" refers to $CO_2$ and sulfur containing compounds, such as $H_2S$, contained in raw shale gas.

The terms "alkane" and "paraffin" are used interchangeably and both refer to any saturated molecule containing hydrogen and carbon atoms only, in which all the carbon-carbon bonds are single bonds and are saturated with hydrogen. Such saturated molecules can be linear, branched, and/or cyclic.

The terms "alkene" and "olefin" are used interchangeably and both refer to any unsaturated molecule containing hydrogen and carbon atoms only, in which one or more pairs of carbon atoms are linked by a double bond. Such unsaturated molecules can be linear, branched, or cyclic, and can include one, two, three or more pairs of carbon atoms linked by double bounds (i.e. mono-olefins, di-olefins, tri-olefins, etc).

The term "hydrocarbon" refers to an organic compound that contains only hydrogen and carbon atoms. The term "Cn" hydrocarbon wherein n is a positive integer, e.g., 1, 2, 3, 4, or 5 or more, means a hydrocarbon molecule having n number of carbon atom(s) per molecule. The term "Cn+" hydrocarbon means a mixture of hydrocarbons containing at least one hydrocarbon having n carbon atoms and at least one hydrocarbon having more than n carbon atoms.

The term "hydrocarbon stream" refers to any stream that naturally contains methane and one or more other hydrocarbons. Illustrative hydrocarbon streams can be or can include a raw shale gas stream or raw natural gas stream or other raw hydrocarbon gaseous stream that is obtained directly (i.e. without processing to remove water and/or acid gas) from a reservoir, wellhead, or pipeline. Suitable hydrocarbon streams can also originate from a refinery, such as from a FCC, coker, steam cracker, and pyrolysis gasoline (pygas). Suitable hydrocarbon streams can also be or can include coal gas. Illustrative hydrocarbon streams can also be or can also include a gas stream that has been treated for acid gas and water removal. For simplicity and ease of description, the detailed description provided herein makes specific references to "shale gas" or "natural gas" or "dry shale gas" or "sweet and dry shale gas"; however, those same references equally apply to any hydrocarbon stream containing at least 50 mol % methane and at least 5 mol % NGL, regardless of how or where the hydrocarbon stream is obtained.

The term "liquid hydrocarbon" refers to a hydrocarbon that is liquid at room temperature and ambient pressure, and primarily includes $C_{5+}$ hydrocarbons. Moreover, this term can also refer to hydrocarbons that are liquid at room temperature but require high pressure such $C_4$ alkane and alkenes.

The term "natural gas liquid" or "NGL" refers to the C2+ alkanes originally contained in a natural gas or shale gas stream, which primarily includes ethane, propane, butane and pentane.

The term "shale gas" refers to natural gas that is produced from a shale or other tight formation, is a gaseous phase mixture containing natural gas liquids, acid gases, water, nitrogen (N2), and possibly trace amounts of contaminants. A suitable shale gas (or natural gas) contains at least 50 mol % $CH_4$ and up to 50 mol % of $C_2H_6$, $C_3H_8$, $C_4H_{10}$, and/or $C_{5+}$ hydrocarbons. For example, a suitable shale gas (or natural gas) contains about 60 mol % to about 95 mol % $CH_4$ and about 5 mol % to about 45 mol % of $C_2H_6$, $C_3H_8$, $C_4H_{10}$, and/or $C_{5+}$ hydrocarbons (or collectively referred to as "$C_{2+}$ hydrocarbons" or "$C_{2+}$ alkanes"). Among the $C_{2+}$ hydrocarbons, $C_2H_6$ is generally the highest concentration followed by $C_3H_8$ then $C_4H_{10}$. Nitrogen gas ($N_2$) can also be present in the shale gas.

The term "sweet shale gas" refers to the shale gas obtained after the acid gases have been removed from the raw shale gas. Only ignorable amount of other components in the raw shale gas is removed together with acid gases and thus, a sweet shale gas has almost all the components contained in raw shale gas except acid gases.

The term "sweet and dry shale gas" refers to the shale gas obtained after the water have been removed from the sweet shale gas. Only ignorable amount of other components in the sweet shale gas is removed together with water and thus, a sweet and dry shale gas has almost all the components contained in raw shale gas except acid gases and water.

The terms "methane ethane cracker", "methane hydrocarbon cracker", "methane cracker", "thermal cracker", "catalytic cracker" and "cracker" are used interchangeably herein. Each term refers to a vessel or other apparatus where a hydrocarbon stream containing one or more paraffins and methane is exposed to heat and/or a catalyst to convert, dehydrogenate, break down, rearrange and/or combine the hydrocarbon molecules of the paraffin(s) to provide one or more olefins.

As used in this application, the term "X" denotes one or more saturated hydrocarbons having two or more carbon atoms including, but not limited to, ethane, propane, butanes, pentanes, higher alkanes, naphtha and mixtures thereof. In addition to its paraffinic hydrocarbon contents, the term "X" also refers to any one or more minor components such as non-paraffinic hydrocarbons and/or non-hydrocarbons which may or may not or may barely participate in the cracking reactions in the cracker but contribute towards enhancing yield of the desired olefin products. These minor components could be 0-15 mol % of the entire mixture denoted by the term "X". Some examples of such minor components include nitrogen, helium and steam.

The term "Y" refers to one or more olefinic hydrocarbon compounds (olefins) including, but not limited to, ethylene, propylene, butene, isobutene, pentenes and mixtures thereof. In addition to its olefin components, components of the mixture denoted by the term "Y" could include unconverted paraffins, unreacted hydrocarbons, unreacted non-hydrocarbons and byproducts associated with the cracking reactions.

The term "wt %" means percentage by weight, "vol %" means percentage by volume, "mol %" means percentage by mole, "ppm" means parts per million, and "ppm wt" and "wppm" are used interchangeably and mean parts per million on a weight basis. All concentrations herein, unless otherwise stated, are expressed on the basis of the total amount of the composition in question.

Each of the appended claims defines a separate invention, which for infringement purposes is recognized as including equivalents to the various elements or limitations specified in the claims. Depending on the context, all references to the "invention" may in some cases refer to certain specific embodiments only. In other cases, it will be recognized that references to the "invention" will refer to subject matter recited in one or more, but not necessarily all, of the claims. Each of the inventions will now be described in greater detail below, including specific embodiments, versions and examples, but the inventions are not limited to these embodiments, versions or examples, which are included to enable a person having ordinary skill in the art to make and use the inventions, when the information in this disclosure is combined with publicly available information and technology.

The following detailed description illustrates embodiments of the present disclosure. These embodiments are described in sufficient detail to enable a person of ordinary skill in the art to practice these embodiments. It should be understood, however, that the embodiments and examples described herein are given by way of illustration only, and not by way of limitation, the embodiments are chosen and described so that others skilled in the art may appreciate and understand the principles and practices of the present teachings. Various substitutions, modifications, additions, and rearrangements can be made that remain potential applications of the disclosed processes. Therefore, the description that follows is not to be taken as limiting on the scope of the appended claims. In particular, an element associated with a particular embodiment should not be limited to association with that particular embodiment but should be assumed to be capable of association with any embodiment discussed herein.

A detailed description will now be provided. The processes provided herein are particularly well suited for hydrocarbon streams that naturally contain methane in addition to one or more other paraffins. Shale gas, condensates or other liquid hydrocarbons are preferred feed streams. Examples of typical hydrocarbon compositions of shale gas and liquid hydrocarbons from three different regions in the United States of America are as shown in Table 1 below. One advantage in using the processes provided herein is that methane is already present in sufficient quantities within these shale streams and can be sent directly to a suitable cracker.

TABLE 1

Typical Shale Wells Compositions from Different Regions in the United States of America

| | Mole Percentage (%) | | |
|---|---|---|---|
| Species | Barnett | Eagle Ford | Bakken |
| Methane ($CH_4$) | 85.5 | 74.3 | 57.8 |
| Ethane ($C_2H_6$) | 6.6 | 13.8 | 20.0 |
| Propane ($C_3H_8$) | 1.9 | 5.4 | 11.4 |
| Butanes ($C_4H_{10}$) | 1.3 | 2.8 | 3.8 |
| Higher Alkanes ($C_{5+}$) | 0.3 | 3.0 | 1.3 |

In general, the processes provided herein allow for the thermal cracking (dehydrogenation) of a paraffin or a mixture of paraffins in the presence of a sufficient quantity of methane, instead of steam, as a diluent. If a feed stream to be dehydrogenated does not have a sufficient quantity of methane, methane can be added to the feed stream prior to cracking.

Figure 3:
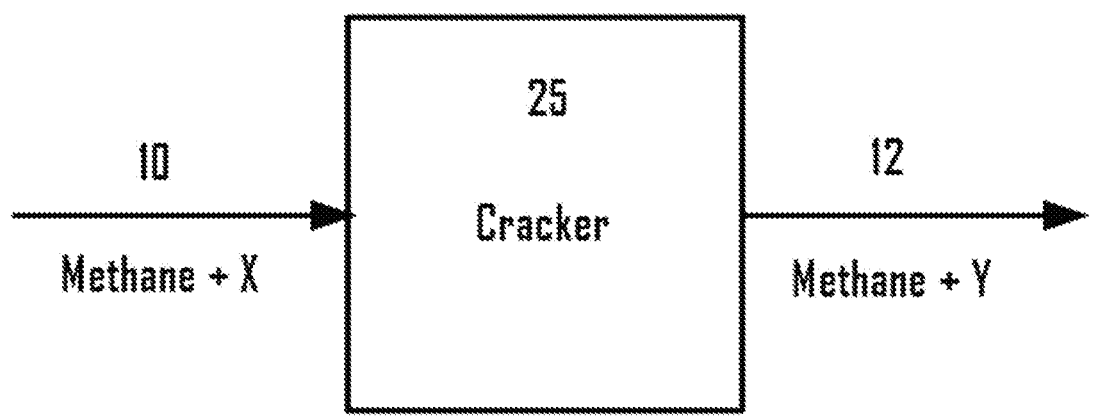
FIG. 3 depicts a flow diagram of an illustrative process for cracking, according to one or more embodiments described herein.

FIG. 3 depicts a flow diagram of an illustrative process for cracking, according to one or more embodiments described herein. An incoming feed or feed stream 10 can be introduced to one or more crackers 25 to provide an exhaust stream 12. If two or more crackers 25 are desired, the crackers 25 can be arranged in parallel or in series. Each cracker 25 be a thermal cracker, catalytic cracker or any combinations thereof.

The feed stream 10 can be any hydrocarbon stream containing a desired amount of methane and one or more other paraffins. The feed stream 10 can be, for example, a mixture of any two or more paraffins (denoted as X) and methane. The desired amount of methane in the feed stream 10 is at least 25 mol %, at least 30 mol %, at least 33 mol %, at least 35 mol %, at least 40 mol %, at least 45 mol %, at least 50 mol %, at least 55 mol %, at least 60 mol %, at least 65 mol %, or at least 75 mol % of methane. The feed stream 10, for example, can include 30 mol % to 95 mol % methane; 35 mol % to 95 mol % methane; 30 mol % to 90 mol %, or 50 mol % to 90 mol %. The feed stream 10 also can include methane ranging in amounts from a low of about 30 mol %, about 33 mol %, or about 35 mol % to a high of about 55 mol %, about 75 mol %, or about 95 mol %. As explained in more detail below, the desired amount of methane in the feed stream 10 can be controlled by adding more methane or by removing methane from the process.

Still referring to FIG. 3, the feed stream 10 can be introduced to the cracker 25 under sufficient reaction conditions towards olefin production. Suitable reaction conditions include temperatures of about 600° C. or more, 700° C. or more, or 800° C. or more and pressure of about 1 atm to 30 atm or about 1 to 20 atm, 2 to 20 atm or 5 to 15 atm. Any suitable cracking furnace known in the art can be used, including those shown in FIG. 2 and those, for example, described in US patents U.S. Pat. No. 5,181,990A and US20090252660A1 using the reaction conditions described therein.

The methane in the feed stream 10 serves as the diluent for the dehydrogenation reaction within the cracker 25. As such, the feed stream 10 and the cracker 25 contain no added steam. The concentration of steam within the cracker 25, therefore, can be about 5 mol % or less; 4 mol % or less; 3 mol % or less; 2 mol % or less; or 1 mol % or less. Preferably, the concentration of steam within the cracker 25 is zero.

In the cracker 25, paraffins are cracked (i.e. dehydrogenated) to form one or more olefins. The residence time in the cracking reactor tubes or coils can be between 0.001 seconds and 10 seconds, and more preferably between 0.005 and 1 second. For a catalytic cracking unit, residence time will depend on the activity of the catalyst.

The exhaust stream 12 from the cracker 25 can be a mixture of methane, one or more olefins and any unreacted paraffin or paraffins (denoted as Y). The exhaust stream 12 can then be sent for further processing, as desired and recognized by those persons skilled in the art.

Figure 4:
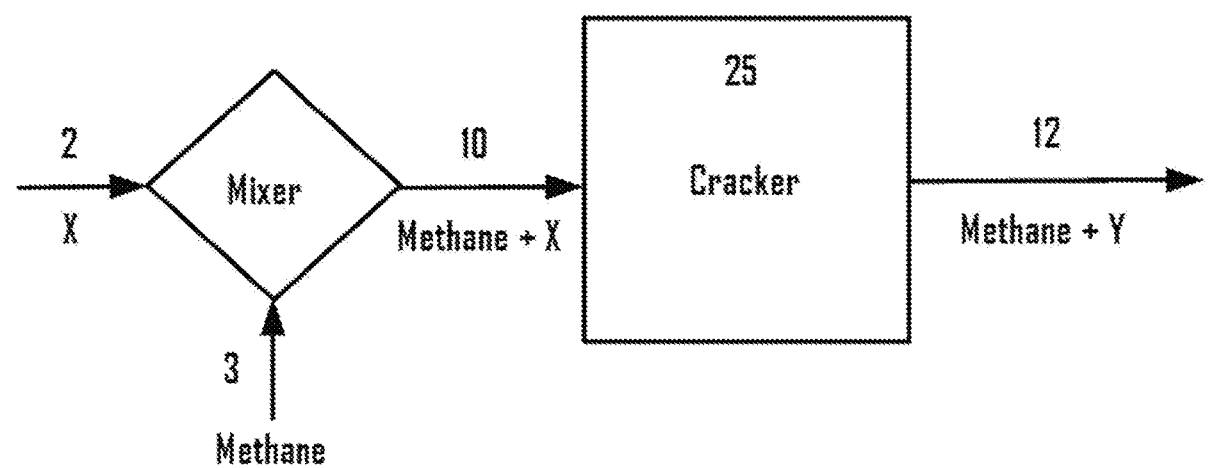
FIG. 4 depicts a flow diagram of another illustrative process for cracking, according to one or more embodiments described herein. As depicted, a methane stream can be added to an incoming methane-free paraffin feed stream to satisfy the feed requirement of the cracker.

FIG. 4 depicts a flow diagram of another illustrative process for cracking, according to one or more embodiments. As depicted, a methane stream 3 can be added to an incoming methane-free paraffin feed stream 2 to satisfy the feed requirement of the cracker 25.

Figure 5:
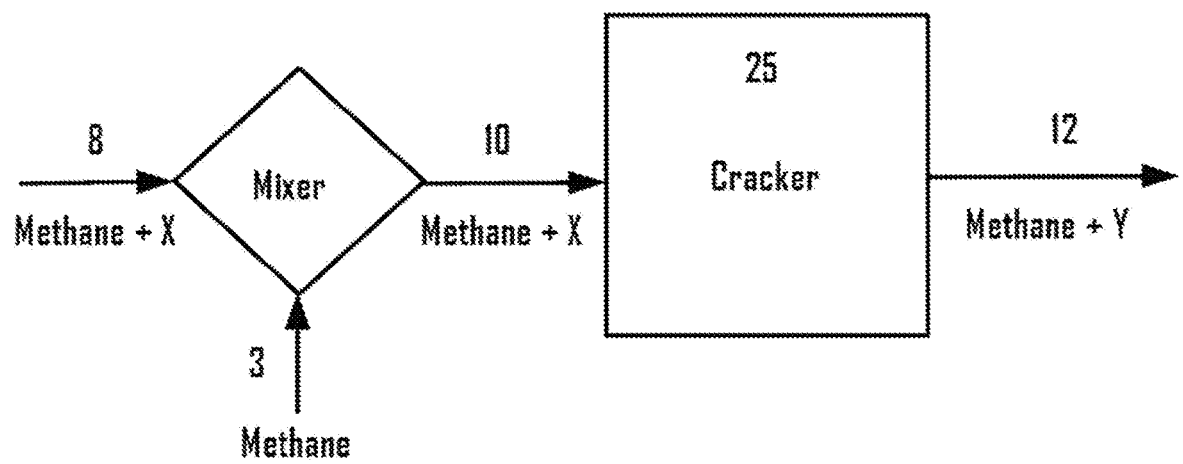
FIG. 5 depicts a flow diagram of another illustrative process for cracking, according to one or more embodiments described herein. As depicted, a methane stream can be added to an incoming paraffin feed containing some, but insufficient amount of methane as needed to satisfy the feed requirement of the cracker.

FIG. 5 depicts a flow diagram of another illustrative process for cracking, according to one or more embodiments described herein. As depicted, a methane stream 3 can be added to an incoming paraffin feed 8 containing some, but an insufficient amount of methane as needed to satisfy the feed requirement of the cracker 25.

Referring to both FIGS. 4 and 5, the combined feed stream 10 provides the needed methane and paraffin(s) mixture in the right proportion for the cracker unit 25. The methane stream 3 can be pure methane or a methane-rich mixture that contains some quantity of one or more other alkanes, olefins and/or any other hydrocarbon and non-hydrocarbon compounds. The fundamental objective is that after mixing, feed stream 10 contains the desired amount of methane as discussed above.

Figure 6:
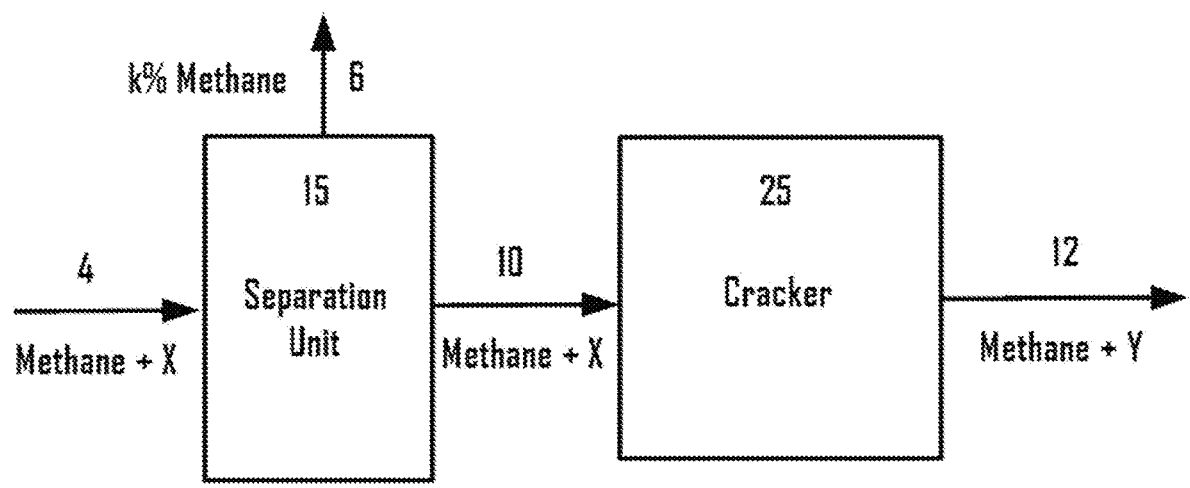
FIG. 6 depicts a flow diagram of yet another illustrative process for cracking, according to one or more embodiments described herein. As depicted, the incoming feed contains excess amount of methane beyond the amount required to satisfy the feed requirement of the cracker. Hence, a prior separation unit is used to remove the excess methane before the feed is sent to the cracker.

FIG. 6 depicts a flow diagram of yet another illustrative process for cracking, according to one or more embodiments If the feed stream 10 contains more methane than needed for economic operation of the cracker 25, it may be attractive to separate a portion of the methane from the given stream. Accordingly, a feed stream 4 can be introduced to one or more separation units 15 to reduce the amount of methane contained therein. The methane can be removed via a methane rich stream 6. As shown, a portion of the methane (denoted as k % of the methane in stream 4) is removed and the remaining stream 10 is sent to the cracker 25. The value of k can be any number depending on the quantity of methane present in the incoming feed stream 4, as well as the cracker design and/or process optimization requirements as may be specified by persons skilled in the art. Stream 10 has most of the paraffin(s) from stream 4. The only missing paraffin(s) portion would be the ones lost in the methane rich stream 6 due to possible inefficiencies in the separation unit 15. The separation unit 15 can be or can include any one or more separation techniques, including but not limited to distillation, membrane, adsorption or absorption.

The cracker 25 can operate at any suitable temperature in the range 500° C. to 1000° C. The temperature of operation will be a function of the type of paraffin or paraffins being present in the feed stream 10 to the cracker 25. For a lighter paraffin such as ethane, a suitable temperature will generally be higher than 700° C. and most preferably from 800° C. to 900° C. For a heavier paraffin, such as butane, the operating temperature will be lower, generally in the range of 500° C. to 700° C. When a mixture of lighter and heavier paraffins are present, the cracking may be performed at higher temperatures suitable for the cracking of lighter paraffins.

The operating pressure in cracker 25 is also a function of the concentration of methane in the feed stream 10. Increase in the methane concentration in the feed stream 10 increases the chances of operating the cracker at high pressures, although lower pressures may still be preferred. Suitable operating pressures will be higher than the atmospheric pressure, and it could be as high as 30 atm.

The cracker unit 25 can be a thermal cracker and contain no catalyst. Thus, as an example, a mixture of methane and ethane in feed stream 10 may be sent to a thermal cracker similar to the currently practiced steam cracker (like the one in FIG. 2) in a temperature range of 800° C.-900° C. with no catalyst. Alternatively, the cracker 25 can be a catalytic cracker. In cases where uses of catalysts enhances the rate of reaction and/or suppresses unwanted side reactions, a catalyst bed may be beneficially used in the cracking unit 25. An example of such a case would be the use of a dehydrogenation catalyst to selectively dehydrogenate a paraffin or a mixture of paraffins in feed stream 10 to one or more olefins. Suitable dehydrogenation catalysts can be or can include platinum-tin (PtSn) catalyst on alumina support, platinum-zinc (PtZn) catalyst on silica support and chromium oxide catalyst on alumina support. Where a catalyst bed (catalysts) is used in the cracking unit 25, the process can be operated adiabatically such that the incoming feed stream 10 provides all the required thermal energy needed to achieve a certain level of conversion within the cracker 25. In which case, the temperature of the flowing fluid continually decreases along the length of the cracking reactor as paraffin(s) conversion progresses. In such circumstances, the use of methane to provide thermal mass for the dehydrogenation process becomes particularly important. The catalyst bed could be designed as a fixed bed, a fluidized bed or a moving bed system, or as may be specified by persons skilled in the art based on process design and/or optimization requirements. Some examples of such catalytic crackers with catalyst bed are the ones described in US patents U.S. Pat. No. 3,978, 150A and US20180154324A1.

From previous discussions, it has been established that the quantity of methane in the feed stream to the cracking unit could be insufficient or in excess. The methane/paraffin ratio of incoming feed stream may need to be adjusted by removal of excess methane or addition of more methane prior to feeding it to the cracker. Accordingly, the typical feeds to be used in the processes provided herein may be classified into the following three categories. In a first and preferred category, the feed is rich in one or more paraffins and contains an adequate amount of methane as per cracker design and/or process optimization requirements as may be specified by someone skilled in the art. In this case, no prior methane separation nor methane addition step is required before passing the feed through the cracker. In a second category, the feed is rich in one or more paraffins but contains an excess amount of methane as per cracker design and/or process optimization requirements as may be specified by someone skilled in the art. In this case, a prior methane separation step would be required before passing the feed through the cracker. In a third category, the feed is rich in one or more paraffins but contains an insufficient amount of methane as per cracker design and/or process optimization requirements as may be specified by someone skilled in the art. In this case, a methane addition step would be required before passing the feed through the cracker.

Figure 2:
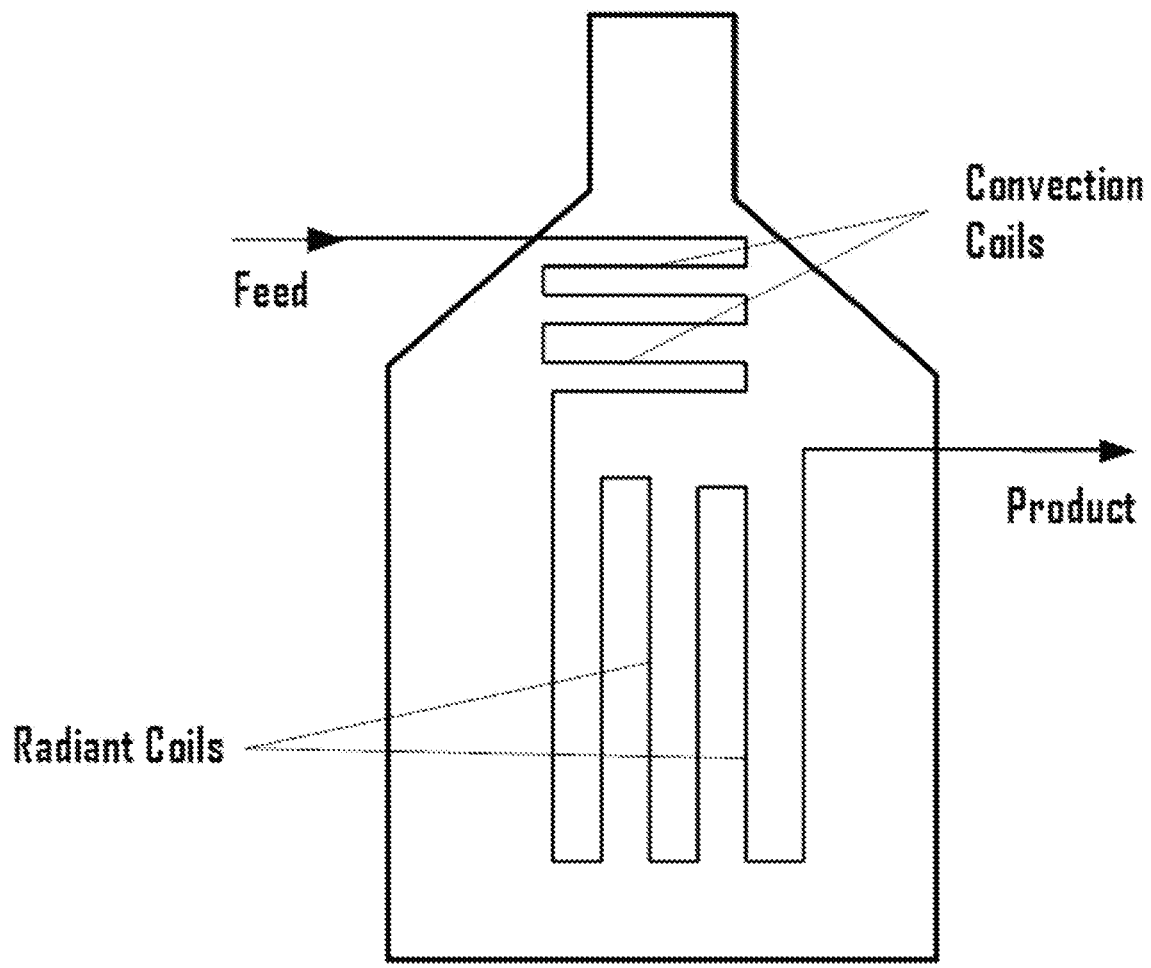
FIG. 2 is a basic diagram of a prior art, conventional cracker furnace as used in the steam cracking process of FIG. 1. A form of this conventional cracker furnace may be used to implement the processes provided herein. Reactions take place in the radiant coil sections of the furnace. The radiant coils could very well also be described as tubular reactors.

Generally, increase in quantity of methane relative to that of paraffins in the feed stream 10 to the cracker unit 25 will have multiple beneficial impacts: (1) for a given operating pressure of the cracker, the partial pressure of the paraffin hydrocarbons will decrease leading to higher levels of dehydrogenation and formation of olefins at the operating temperature of the cracker; (2) it will be possible to increase the operating pressure of the cracker while keeping partial pressure of paraffins at reasonably low pressures, and thereby obtain reasonable levels of paraffins conversions while keeping pressure drop losses due to stream flows low; and (3) when the cracker is an adiabatically operated catalytic reactor unit, the increase in methane concentration will provide increased thermal energy for the dehydrogenation process and for the same temperature change across the catalytic cracker, one will achieve corresponding increase in paraffin(s) conversions to olefin(s). On the other hand, for a given quantity of paraffins to be processed, increases in methane concentration in feed stream 10 to the cracker 25 increases mass flow. This means that a greater quantity of mass needs to be processed through the cracker 25 and downstream equipment. Therefore, depending on the feed stream 10 being processed, an economic optimum in the concentration of methane will likely exist. This optimum will also depend on whether a conventional thermal cracking unit of the type shown in FIG. 2 is employed or an adiabatic catalytic cracker is used, with the later benefiting more from an increased methane concentration.

Figure 7:
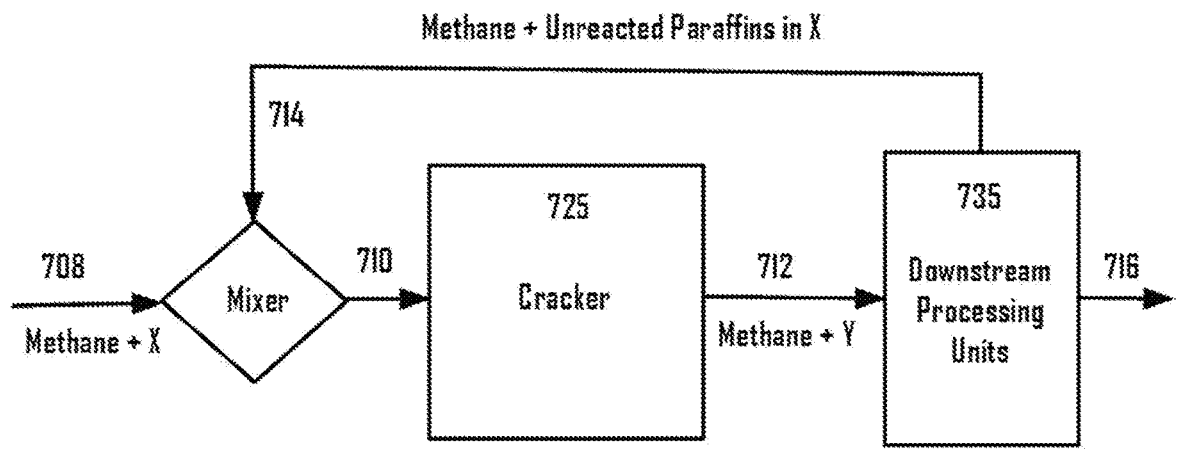
FIG. 7 depicts a flow diagram of yet another illustrative process for cracking, according to one or more embodiments described herein. As depicted, the incoming feed can be sent through the cracker, and any unconverted paraffins can be recycled together with an option of adding an adequate amount of methane back to the cracker after subsequent downstream processing.

FIG. 7 depicts a flow diagram of yet another illustrative process for cracking, according to one or more embodiments. As depicted, stream 712 exiting the cracker 725 can contain methane, unreacted paraffins and useful olefin product and can be processed in one or more downstream processing units 735. From at least one of the downstream units 735, a stream 714 containing unreacted paraffins can be obtained, and can be recycled and combined with the stream 708 to provide the feed stream 710 for the cracker 725. Streams 708 and 710 can be the same or similar to streams 8 and 10, respectively, as discussed above.

Through the recycle stream 714, unreacted paraffins can be re-introduced to the cracker 725 and dehydrogenated, forming more olefins. Additionally, through stream 714, along with unreacted paraffins, some methane can be recycled. The advantage of methane in the recycle stream 714 is that it helps to adjust the quantity of methane in the feed 710 to the cracker unit 725. This recycle of methane through stream 714 is also valuable when there is little to no methane in the feed stream 708.

There is likely to be multiple product streams from the downstream processing units 735 and stream 716 represents all such streams. For example, with methane present in feed stream 708, a methane-rich stream will be produced as a byproduct through the downstream processing units 735 to avoid build-up of methane in the cracker 725 due to recycle stream 714. Such a methane-rich byproduct stream will form part of the multiple product streams represented by stream 716.

Figure 8:
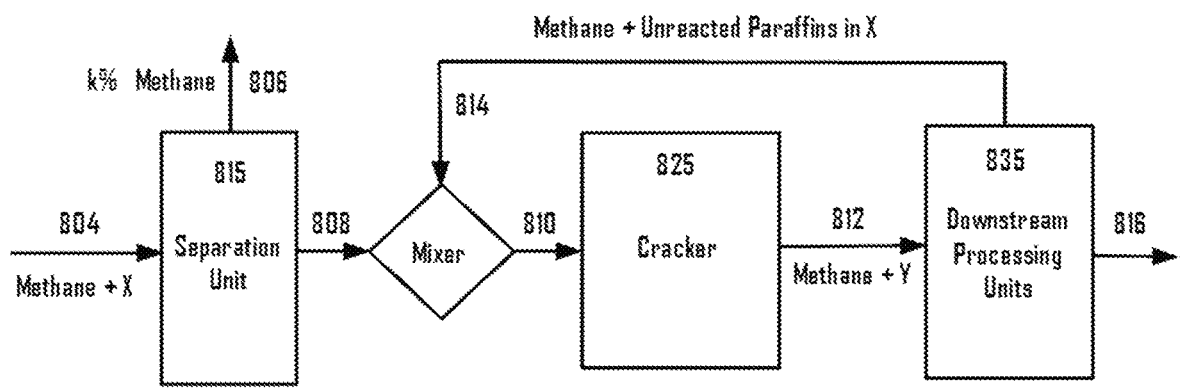
FIG. 8 depicts a flow diagram of yet another illustrative process for cracking, according to one or more embodiments described herein. As depicted, an excess portion of the methane can be separated from the incoming feed, before sending the feed to the cracker. After subsequent processing downstream of the cracker, any unconverted paraffins, optionally with an adequate amount of methane, can be recycled back to the cracker.

FIG. 8 depicts a flow diagram of yet another illustrative process for cracking, according to one or more embodiments described herein. This process in FIG. 8 incorporates embodiments from FIGS. 6 and 7. Stream 804 is the same or similar to stream 4. Stream 808 is the same or similar to stream 8. Stream 810 is the same or similar to stream 10. Different from those embodiments depicted in FIGS. 6 and 7 is that any unconverted paraffins from the downstream processing units 835 can be recycled to the cracker 825 via stream 814 to achieve a higher yield of olefins from the paraffins in the feed stream 804. The recycle stream 814 can also contain methane. It is possible that the combined methane from the feed stream 804 and the recycle stream 814 can lead to more than a desired amount of methane to the cracker 825. To reduce the methane concentration, if need be, some fraction of methane can be removed via stream 806 from the feed 804 in separation unit 815. The downstream processing units 735 and 835 can be or can include, any one or more, separation units, reactor units, heat transfer units, compression units and combinations thereof.

Methane is mostly an inert at temperatures of 1,000° C. or more. This property of methane makes it particularly suitable as a replacement option for steam in the thermal cracking of paraffin to produce olefin. Just as with steam, the presence of methane as a diluent in the feed to the cracker helps to reduce the paraffin (reactant) partial pressure and provide thermal mass for the paraffin dehydrogenation reaction. In this way, reactor productivity is enhanced and reactants conversions as well as products (olefins) yields are improved. Whereas liquid water has to be converted to steam before it can be used as a diluent in a steam cracker and has high latent heat that must be supplied, methane need not undergo any such phase change before it can be similarly used in the processes provided herein. Accordingly, the complex and expensive high-temperature steam generation steps that are associated with steam cracking are eliminated by replacing steam with methane. Furthermore, the complexities and high energies associated with the use of steam limit the amount of steam that can be used in the steam cracker.

To increase the quantity of steam to be used in a steam cracker requires bigger steam generation equipment and much higher quantities of heat associated with the vaporization of increased quantities of water to the vapor state. Consequently, there is a limit on the overall pressure at which the steam cracker can be operated as the partial pressure of the paraffins must be kept low for reasonable conversions. Such limitations do not arise with the use of methane. It is possible to use very high concentration of methane in the feed to the cracker without concern regarding associated costs for methane generation. This makes it feasible to run the crackers 25, 725, 825 at higher pressures while keeping the partial pressures of paraffins low in the feed 10, 710, 810.

EXAMPLES

The foregoing discussion can be further described with reference to the following non-limiting examples.

Example 1

Equilibrium conversions of ethane to ethylene at the cracker temperatures of 850° C. and pressure of 2.2 atm were obtained under different conditions using Aspen Plus to perform the equilibrium calculations. It should be noted that equilibrium conversion is a reflection of the potential of a process in terms of its achievable maximum conversion for a given set of operating conditions. The higher the equilibrium conversion, the higher the actual paraffin conversion that can be achieved per pass through the cracker. Table 2 provides equilibrium conversions for a pure ethane feed, a conventional steam ethane cracker feed and various mixtures with different methane to ethane mole ratios at a temperature of 850° C. and pressure of 2.2 atm.

TABLE 2

| Feed Ratio | Equilibrium Conversion |
| --- | --- |
| Pure Ethane | 72.7% |
| 0.35 Kg Steam/1 Kg Ethane | 76.4% |
| 0.5 Mol $CH_4$/0.5 Mol $C_2H_6$ | 78.5% |
| 0.6 Mol $CH_4$/0.4 Mol $C_2H_6$ | 80.7% |
| 0.7 Mol $CH_4$/0.3 Mol $C_2H_6$ | 83.5% |
| 0.8 Mol $CH_4$/0.2 Mol $C_2H_6$ | 87.3% |
| 0.9 Mol $CH_4$/0.1 Mol $C_2H_6$ | 92.5% |

It should be noted that typical conditions for a commercial steam ethane cracker include a temperature of 850° C., pressure of 2.2 atm and steam to ethane ratio of 0.35 Kg steam/1 kg ethane (these are also the conditions employed for the calculations in Table 2). At these conditions for the steam ethane cracker, the actual conversions of ethane obtained commercially are about 65%, as reported by Zimmermann H. and Walzl R. in "*Ullmann's Encyclopedia of Industrial Chemistry on Ethylene*", whereas the calculated equilibrium conversion was 76.4% as reported above in Table 2. We observe from this table that a methane and ethane mixture according to the processes provided herein is capable of providing much higher ethane conversions than the steam cracker. A 50 mol % methane in the feed has the potential to provide similar actual ethane conversion as the conventional steam ethane cracker while increasingly improving conversion performance as methane concentration increases to 90%.

For all the different cases of methane/ethane molar ratio illustrated in Table 2, the methane ethane cracker outperforms the steam ethane cracker in terms of ethane conversion. As has been earlier established, increasing the quantity of the diluent steam for the steam ethane cracker implies additional processing cost in terms of steam generation, which is not the case with methane. As shown in Table 1, most gas streams from shale wells have methane present in them and can be fed to the cracker directly or after adequate adjustment to achieve the desired methane concentration. Table 1 also shows that for feeds from the three shale well regions, it is possible to have methane to ethane molar ratio in the feed to the cracker in the range shown in Table 2.

Example 2

Table 3 shows equilibrium conversion of ethane for a thermal cracker operating at a temperature of 850° C. and pressure of 5 atm. It is observed that at a higher operating pressure of 5 atm, the feeds to the cracker with 80 mol % methane and 90 mol % methane have promises to provide same or even higher level of ethane conversion per pass as the conventional steam cracker case operating at 2.2 atm and same temperature (Table 2). Clearly, the use of methane enables the use of higher pressures while retaining comparable or achieving better conversions of ethane compared to the steam cracker operating at lower pressures.

TABLE 3

| Feed Ratio | Equilibrium Conversion |
| --- | --- |
| Pure Ethane | 57.4% |
| 0.35 Kg Steam/1 Kg Ethane | 61.3% |
| 0.8 Mol $CH_4$/0.2 Mol $C_2H_6$ | 75.7% |
| 0.9 Mol $CH_4$/0.1 Mol $C_2H_6$ | 84.6% |

Example 3

Table 4 shows equilibrium conversion of ethane to ethylene for a thermal cracker operating at a temperature of 850° C. and pressure of 15 atm. Even under such a high pressure of operation, with 90 mol % of methane in the feed to the cracker, reasonable conversion of ethane can be obtained. Note the predicted relatively poor performance of a steam cracker operating at same temperature of 850° C. and pressure of 15 atm with 0.35 kg steam/1 kg ethane.

TABLE 4

| Feed Ratio | Equilibrium Conversion |
| --- | --- |
| Pure Ethane | 37.48% |
| 0.35 Kg Steam/1 Kg Ethane | 40.0% |
| 0.8 Mol $CH_4$/0.2 Mol $C_2H_6$ | 52.97% |
| 0.9 Mol $CH_4$/0.1 Mol $C_2H_6$ | 65.34% |

Example 4

Table 5 shows the equilibrium conversion of another paraffin (propane) for a thermal cracker operating at 600° C. and 2 atm as a demonstration of the applicability of the processes provided herein to different types of paraffin feed.

Table 5 provides equilibrium conversions for a pure propane feed and various mixtures with different methane to propane molar ratios according to the processes provided herein. Just as observed for the case with ethane conversion in Table 2, the potential for higher conversions of propane through the cracker increases as the concentration of methane increases.

TABLE 5

| Feed Ratio | Equilibrium Conversion |
|---|---|
| Pure Propane | 46.0% |
| 0.6 Mol $CH_4$/0.4 Mol $C_3H_8$ | 61.1% |
| 0.7 Mol $CH_4$/0.3 Mol $C_3H_8$ | 66.6% |
| 0.8 Mol $CH_4$/0.2 Mol $C_3H_8$ | 74.1% |
| 0.9 Mol $CH_4$/0.1 Mol $C_3H_8$ | 84.6% |

Based on the foregoing, it should be apparent to those of ordinary skill in the art that the processes provided herein have the potential for significant savings in capital and operating costs in the construction and operation of a thermal cracking plant for olefin production. This is in addition to the great simplicity associated with the process. The processes provided herein eliminate the expensive and complex steps associated with steam generating and handling for steam cracking. The processes provided herein would be particularly well suited for modular processing and distributed manufacturing towards olefin production.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, meaning the values take into account experimental error, machine tolerances and other variations that would be expected by a person having ordinary skill in the art.

The foregoing has also outlined features of several embodiments so that those skilled in the art can better understand the present disclosure. Those skilled in the art should appreciate that they can readily use the present disclosure as a basis for designing or modifying other methods or devices for carrying out the same purposes and/or achieving the same advantages of the embodiments disclosed herein. Those skilled in the art should also realize that such equivalent constructions do not depart from the spirit and scope of the present disclosure, and that they can make various changes, substitutions, and alterations herein without departing from the spirit and scope of the present disclosure, and the scope thereof is determined by the claims that follow.

Various terms have been defined above. To the extent a term used in a claim is not defined above, it should be given the broadest definition persons in the pertinent art have given that term as reflected in at least one printed publication or issued patent. Furthermore, all patents, test procedures, and other documents cited in this application are fully incorporated by reference to the extent such disclosure is not inconsistent with this application and for all jurisdictions in which such incorporation is permitted.

What is claimed is:

1. A process for converting paraffins to olefins, comprising:
obtaining a feed stream comprising naturally occurring methane and one or more paraffins, wherein the feed stream comprises 30 mol % to about 95 mol % of the naturally occurring methane;
passing the feed stream containing the naturally occurring methane and one or more paraffins to a cracker;
converting at least a portion of the one or more paraffins to one or more olefins within the cracker in the presence of the naturally occurring methane to provide a product stream comprising the one or more olefins.

2. The process of claim 1, further comprising removing sour gas from the feed stream prior to passing the feed stream to the cracker, wherein the feed stream after sour gas removal comprises the same naturally occurring methane and same one or more paraffins as the feed stream prior to the sour gas removal.

3. The process of claim 1, wherein the naturally occurring methane and one or more paraffins are derived directly from a wellhead, reservoir, or pipeline.

4. The process of claim 1, wherein the cracker operates at a temperature of 500° C. to about 1,000° C., and a pressure of about 1 atm to about 30 atm.

5. The process of claim 1, wherein the one or more paraffins are converted to one or more olefins in the presence of a catalyst.

6. The process of claim 1, further comprising separating at least a portion of the naturally occurring methane from the feed stream prior to passing the feed stream to the cracker to adjust the amount of the naturally occurring methane in the feed stream entering into the cracker.

7. The process of claim 1, further comprising separating at least a portion of the methane from the product stream and recycling the separated methane to the feed stream prior to passing the feed stream to the cracker.

8. The process of claim 1, wherein the one or more paraffins are converted to one or more olefins in the absence of catalyst.

9. The process of claim 1, wherein the cracker contains a catalyst bed.

10. The process of claim 9, wherein the catalyst bed is a fixed bed, fluidized bed or moving bed.

11. The process of claim 1, wherein the feed stream further comprises less than 15 mol % of one or more non-paraffinic hydrocarbons and/or non-hydrocarbons.

12. The process of claim 11, wherein the non-hydrocarbons comprise nitrogen, helium, steam, or a mixture thereof, and wherein the one or more paraffins comprise ethane, propane, butane, pentane, naphtha or any combinations thereof.

13. The process of claim 1, wherein the methane concentration in the feed stream is about 30 mol % to about 90 mol %.

14. The process of claim 1, wherein methane concentration in the feed stream is about 50 mol % to about 90 mol %.

15. The process of claim 1, wherein the feed stream and cracker have no added steam.

16. A process for converting paraffins to olefins, comprising:
obtaining a feed stream comprising naturally occurring methane and one or more paraffins, wherein the feed stream comprises 30 mol % to about 95 mol % of the naturally occurring methane;

removing sour gas from the feed stream, wherein the feed stream after sour gas removal comprises the same naturally occurring methane and same one or more paraffins as the feed stream prior to the sour gas removal;

passing the feed stream containing naturally occurring methane and one or more paraffins to a cracker, wherein the feed stream comprises 30 mol % to about 95 mol % of the naturally occurring methane and less than 5 mol % steam;

converting at least a portion of the one or more paraffins to one or more olefins within the cracker to provide a product stream comprising the one or more olefins.

17. The process of claim 16, wherein the cracker operates at a temperature of 500° C. to about 1,000° C., and a pressure of about 1 atm to about 30 atm.

18. The process of claim 16, wherein the residence time through the tubes is between 0.001 to 10 seconds.

19. The process of claim 16, further comprising separating at least a portion of the naturally occurring methane from the feed stream prior to passing the feed stream to the cracker.

20. The process of claim 19, further comprising separating methane from the product stream and recycling at least a portion of the separated methane to the feed stream prior to passing the feed stream to the cracker.

* * * * *